US005699920A

United States Patent [19]

Ida et al.

[11] Patent Number: 5,699,920

[45] Date of Patent: Dec. 23, 1997

[54] PUMP NURSER FOR EXPELLING AIR FROM DISPOSABLE LINERS

[76] Inventors: Frank Ida, 1 Jillit Dr., Smithtown, N.Y. 11787; Luciano DiScala, 111 Arpage Dr. East, Shirley, N.Y. 11967

[21] Appl. No.: 517,709

[22] Filed: Aug. 21, 1995

[51] Int. Cl.$^{6}$ .............................. A61J 9/04

[52] U.S. Cl. .................. 215/11.3; 215/11.5; 222/386.5; 222/490

[58] Field of Search .................. 215/11.3, 11.5, 215/11.1; 222/105, 386.5, 490, 212, 213, 107

[56] References Cited

U.S. PATENT DOCUMENTS

| | | | |
|---|---|---|---|
| 2,846,103 | 8/1958 | Maxwel | 215/11.3 |
| 2,987,209 | 6/1961 | Leonard | 215/11.3 |
| 3,292,808 | 12/1966 | Greene | 215/11.5 |
| 3,511,407 | 5/1970 | Palma | 215/11.7 |
| 3,718,140 | 2/1973 | Yamauchi | 215/11.1 |
| 3,768,682 | 10/1973 | Meyers et al. | 215/11.5 |
| 4,176,754 | 12/1979 | Miller | 215/11.1 |
| 4,241,768 | 12/1980 | Keller et al. | 215/11.3 X |
| 4,295,582 | 10/1981 | Acres | 222/213 |
| 4,401,224 | 8/1983 | Alonso | 215/11.5 |
| 4,730,744 | 3/1988 | Vinciguerra | 215/11.5 |
| 4,842,165 | 6/1989 | Van Coney | 222/105 X |
| 4,880,125 | 11/1989 | LeBeau | 215/11.3 |
| 5,318,204 | 6/1994 | Davis et al. | 222/105 X |
| 5,356,016 | 10/1994 | Wiedemann | 215/11.3 |
| 5,524,783 | 6/1996 | Popoff | 215/11.1 X |

*Primary Examiner*—Gary E. Elkins
*Assistant Examiner*—Christopher J. McDonald

[57] ABSTRACT

The nurser is made of a resilient outer shell and a flexible liner. A nipple is attached to the upper end of the outer shell. The outer shell is squeezed to allow the pressure inside to increase and force air in the liner through the nipple. The nurser utilizes a one way valve on the outer shell to allow air into the shell when the pressure is released from the outer shell. This prevents the liner from expanding and air from reentering the liner.

4 Claims, 3 Drawing Sheets

PUMP NURSER FOR EXPELLING AIR FROM DISPOSABLE LINERS

BACKGROUND OF THE INVENTION

The invention related to a method of removing air that is trapped in a disposable liner of a nurser. Air which is trapped in the liner is often ingested by the baby feeding from the nurser. This air ends up in the baby's stomach and can cause pain and regurgitation. The elimination of the air from the liner prevents the baby from ingesting the air and so reduces the possibility of the negative side effects associated with air in the baby's stomach.

The problem of air in a disposable liner has been recognized for some time. The prior art discloses devices which are used to eliminate air from the liner. The prior art has used plungers, such as those disclosed in U.S. Pat. No. 5,524,783 to Popoff; U.S. Pat. No. 4,880,125 to LeBleau and U.S. Pat. No. 3,648,873 to Grobbel. These devices comprise plungers connected to bases. The end of the plunger is used to mechanically collapse the liner toward the nipple on the nursers. This causes a decrease in volume of the liner. As the liquid in the liner moves upward in response to the mechanical pressure from the plunger, the air in the liner is expelled through the nipple. A similar device is disclosed in U.S. Pat. No. 4,176,745 to Miller that has a pneumatic member(12) that applies a force to a liner to insure that there is no air in the liner. A problem with these devices is that, if the plunger or pneumatic member is removed, there is nothing to prevent the liner from expanding and air being reintroduced into the bag. This would necessitate that the liner again be collapsed to expel the air before the nurser is used to feed a baby.

Many nursers use disposable liners in the nurser. These liners provide for easy cleaning as they are simply thrown away and replaced. Many of these nursers have apertures in the bottom. These apertures allow air into the bottle to collapse the liner as the baby takes liquid from the nurser. This allows the pressure around the liner to be equal to the pressure outside of the nurser. Examples of these types of nursers are U.S. Pat. No. 2,987,209 to Leonard and U.S. Pat. No. 2,846,103 to Maxwell. Some nursers employ valves on the bottom of the nurser. These nursers do not use liners. Some examples of these types of nursers are U.S. Pat. No. 3,768,682 to Myers et al., U.S. Pat. No. 3,292,808 to Greene and U.S. Pat. No. 3,511,407 to Palma. The valves allow air to enter the bottle to replace the volume of liquid that is consumed by the baby during feeding. The valve opens when the pressure in the bottle is less than the pressure out of the bottle. The valve prevents the liquid in the bottle from leaking when the bottle is in the upright position.

SUMMARY OF THE INVENTION

The invention utilizes pneumatic pressure on the liner to collapse the liner and force the air through the nipple. This pressure is generated by using the nurser's shell body as the pump. The pressure is maintained at above atmospheric levels by sealing the aperture in the shell body with a one way valve. This allows the nurser to maintain the pressure, and therefor the liner in its collapsed state, even when the nurser is left unattended.

It is an object of the invention to provide a nurser that removes the air from a liner and prevents air from being reintroduced.

It is another object of the invention to provide a nurser that can remove air from a nurser without the need for any device that is not part of the nurser.

It is another object of the invention to provide a nurser that is easy to use and operate.

DETAILED DESCRIPTION OF THE INVENTION

Figure 1:
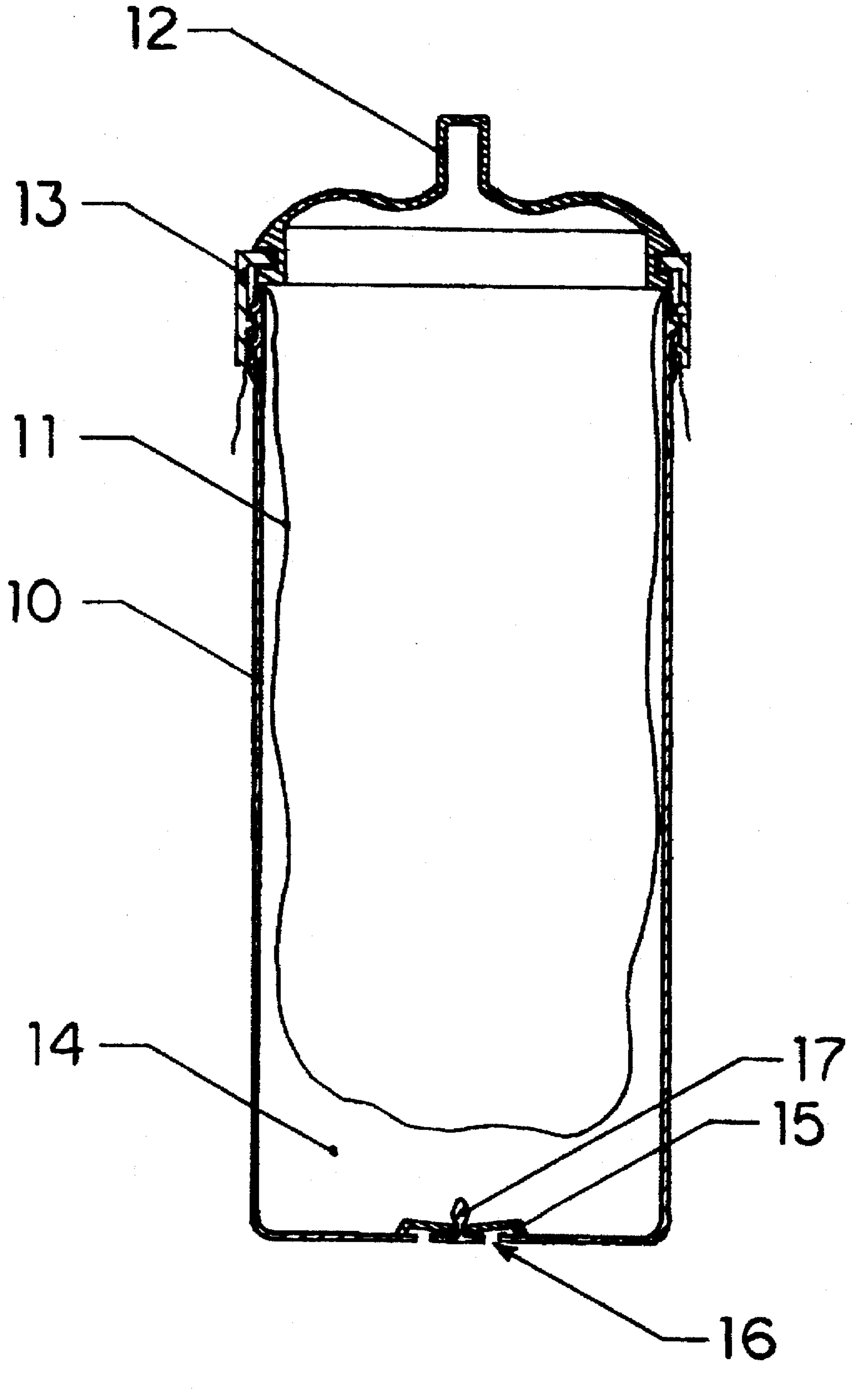
FIG. 1 shows a cross section view of the nurser.
Figure 3:
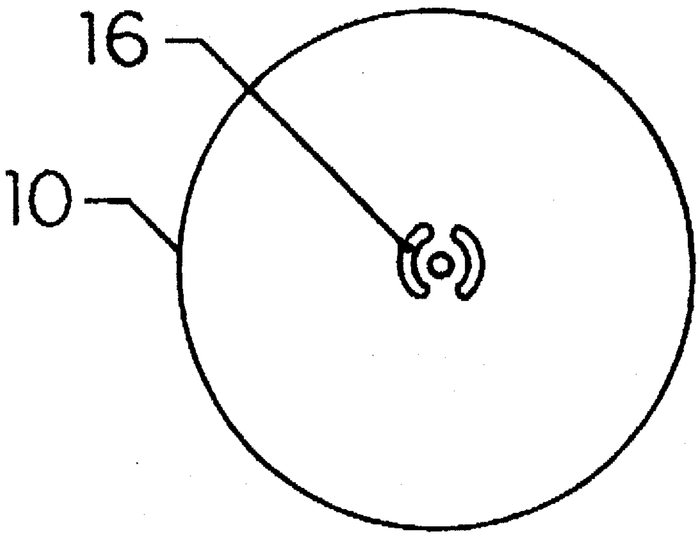
FIG. 3 is a bottom view of the nurser.
Figure 2:
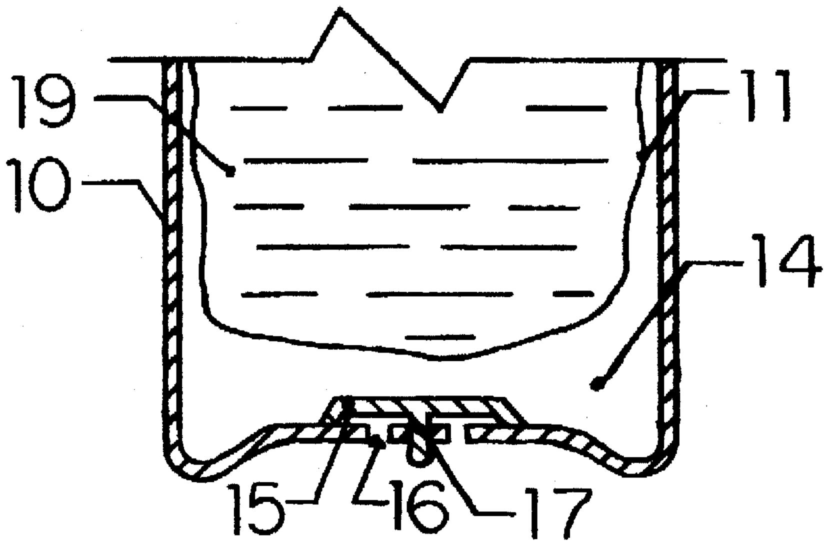
FIG. 2 shows the detail of the lower half of the nurser.

Referring to FIGS. 1 to 3, the structure of the nurser can be seen. The nurser has a resilient shell body 10 that has an open top end and a bottom end that has an aperture 16. The aperture 16 is sealed with an air flow check valve 15. The air flow check valve is made from silicone rubber. A projection 17 of the shell body 10 or air flow check valve 15 connects the air flow check valve 15 to the shell body 10. The top end of the shell body is connected to a nipple 12 that has an orifice 18. The nipple 12 may be of the self sealing type. The nipple 12 is connected to the shell body by a retaining ring 13. The retaining ring 13 has threads that mate with threads on the shell body. Retained between the mating threads is a liner 11 that holds liquid 19 that is to fed to the baby. The space between the liner and shell body creates a chamber 14.

Figure 4:
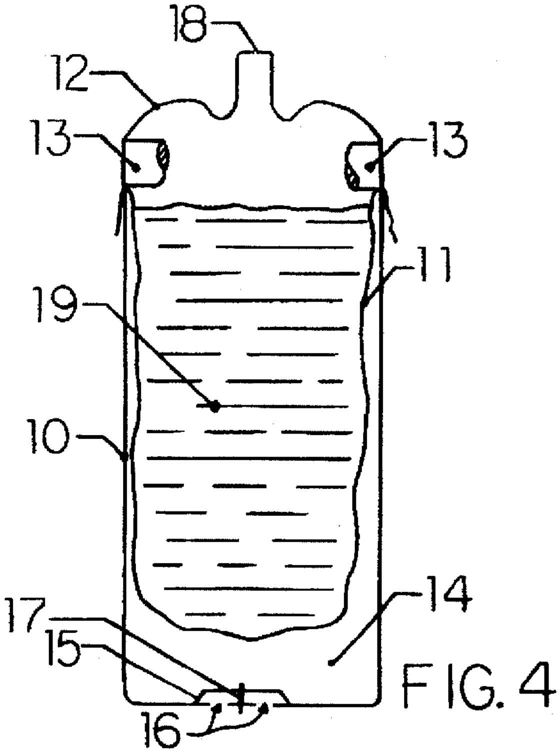
FIG. 4 shows the initial state of the nurser with air in the liner.
Figure 5:
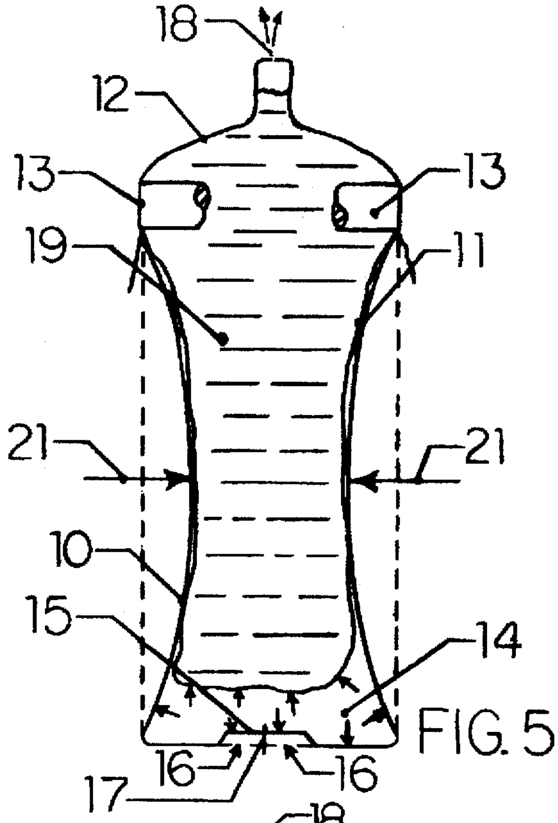
FIG. 5 shows the nurser being squeezed with the liquid in the liner rising and the air being expelled from the liner.

The operation of the nurser is best explained by referring to FIGS. 4 through 7. FIG. 4 shows the nurser with a liner 11 filled with liquid 19 and having air trapped inside of it. The shell body 10 is in its normal state. FIG. 5 shows the nurser as pressure 21 is applied to the shell body 10. The shell body 10 is in its collapsed state. As the shell body 10 is collapsed, the size of the chamber 14 decreases. Air cannot escape the chamber through the air flow check valve 16 because the pressure does not cause the valve 16 to open. The pressure in the chamber 14 acts on the liner 11 to cause the liquid 19 in the liner to rise. This causes the air in the liner to be expelled through the nipple orifice 18.

Figure 6:
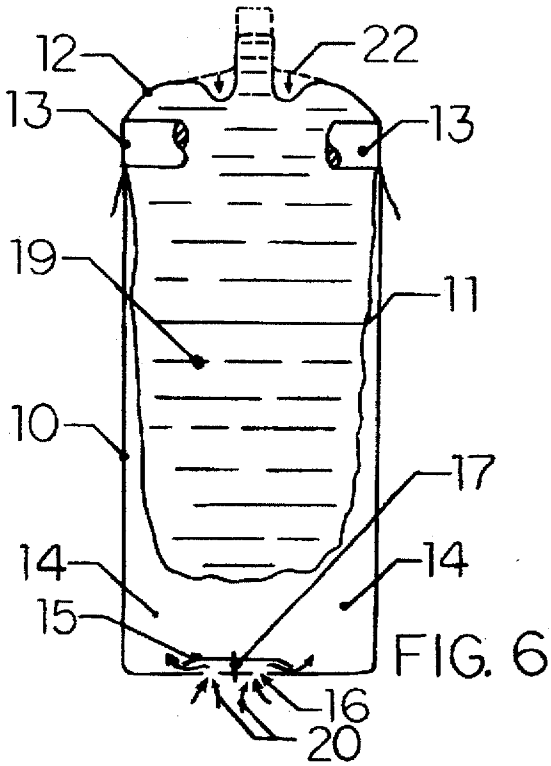
FIG. 6 shows the nurser's shell body expanding as air enters through the aperture in the shell body.
Figure 7:
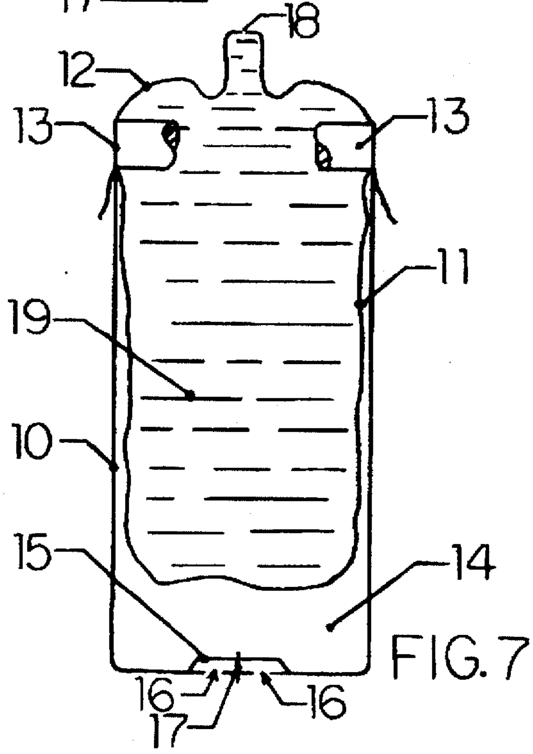
FIG. 7 shows the nurser's shell body returned to its original state with the aperture sealed and no air in the liner.

Turning now to FIG. 6, the operation of the bottle when the pressure is released can be seen. Since the liner was collapsed and the air in the liner expelled, the liner occupies a smaller volume that is previously did before pressure was applied. The result is that chamber 14 will be bigger than it was previously. As the shell body 10 expands, the pressure in the chamber 14 decreases as its volume increases. When the volume of the chamber gets to be bigger than it was in its original state (before the pressure was applied), the pressure falls below the pressure outside the shell body 10. This pressure differential causes the air flow check valve to open and air 20 to enter the chamber. When the pressure 21 is released, the nipple returns to its original shape as can be seen by the phantom lines 22. When enough air has entered to account for the chamber's increased volume, the air check flow valve closes. This is seen in FIG. 7.

After this process, the resulting state is a liner that has no air and a chamber 14 that has enough pressure to prevent the weight of the liquid 19 in the liner 11 from causing the liner to expand, thereby allowing air back into the liner 11. As can be seen, the nurser can be put down and unattended without air being reintroduced into the liner 11. As the baby feeds from the liner 11, the volume of the liner 11 decreases and the volume of the chamber increases 14. When the chamber's volume increases a sufficient amount to cause a pressure differential, the air flow check valve 16 will again open to allow air into the chamber 14. In this regard, it works similarly to the prior art nursers that have a one way valve and no liner.

We claim:

1. A method of feeding an infant with a bottle, comprising;

providing a bottle, the bottle having a resilient shell body having an open top end and an aperture, a nipple attached to the shell body top end, a air flow check valve over the aperture, a flexible liner suspended from the shell body top end creating a chamber between the liner and shell body, filling the flexible liner, applying pressure to the shell body to collapse the shell body and force air in the liner through the nipple, releasing the pressure to the shell body and allowing air to enter the chamber through the air flow check valve, the air preventing the liner from expanding and allowing air to enter the liner through the nipple, feeding the bottle to an infant.

2. The method of claim 1 wherein the nipple is attached to the shell body by a retaining ring.

3. The method of claim 1 wherein the nipple is self sealing.

4. The method of claim 1 wherein the air flow check valve is made from silicone rubber.

* * * * *